United States Patent
Jirsa et al.

(10) Patent No.: US 12,232,883 B2
(45) Date of Patent: Feb. 25, 2025

(54) METHOD OF MODULATING EPILEPTOGENICITY IN A PATIENT'S BRAIN

(71) Applicants: UNIVERSITE D'AIX MARSEILLE (AMU), Marseilles (FR); CENTRE NATIONAL DE LA RECHERCHE SCIENTIFIQUE (CNRS), Paris (FR); ASSISTANCE PUBLIQUE—HOPITAUX DE MARSEILLE (AP-HM), Marseilles (FR); INSTITUT NATIONAL DE LA SANTE ET DE LA RECHERCHE MEDICALE (INSERM), Paris (FR)

(72) Inventors: Viktor Jirsa, Marseilles (FR); Christophe Bernard, Marseilles (FR); Fabrice Bartolomei, Roquevaire (FR); Maxime Guye, Saint Cyr sur Mer (FR)

(73) Assignees: UNIVERSITE D'AIX MARSEILLE (AMU), Marseilles (FR); CENTRE NATIONAL DE LA RECHERCHE SCIENTIFIQUE (CNRS), Marseilles (FR); ASSISTANCE PUBLIQUE—HOPITAUX DE MARSEILLE (AP-HM), Marseilles (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 735 days.

(21) Appl. No.: 17/510,182

(22) Filed: Oct. 25, 2021

(65) Prior Publication Data
US 2022/0039736 A1 Feb. 10, 2022

Related U.S. Application Data

(62) Division of application No. 16/316,803, filed as application No. PCT/IB2016/001164 on Jul. 18, 2016, now Pat. No. 11,191,476.

(51) Int. Cl.
*A61B 5/00* (2006.01)
*A61B 5/291* (2021.01)
(Continued)

(52) U.S. Cl.
CPC ............ *A61B 5/4094* (2013.01); *A61B 5/291* (2021.01); *A61B 5/369* (2021.01); *A61B 34/10* (2016.02);
(Continued)

(58) Field of Classification Search
CPC ....... A61B 5/4094; A61B 5/291; A61B 5/369; A61B 34/10; A61B 2034/101; A61B 2034/105; G16H 50/50; G16H 10/60
See application file for complete search history.

(56) References Cited

U.S. PATENT DOCUMENTS 9,687,163 B2 6/2017 Han et al.
2014/0128762 A1* 5/2014 Han ..................... A61B 5/4064
600/544

(Continued)

FOREIGN PATENT DOCUMENTS

EP 3 235 427 A1 10/2017
GB 2541427 A 2/2017
(Continued)

OTHER PUBLICATIONS

Proix, "Seizure spread in a virtual epileptic patient", Seventh International Workshop on Seizure Prediction, www.youtube.com/watch?v=PwOVMmRmMEo, Dec. 9, 2015 (retrieved Apr. 13, 2017); 19 pages; cited in the ISR of parent U.S. Appl. No. 16/316,803; parent U.S. Appl. No. 16/316,803.
(Continued)

*Primary Examiner* — Carrie R Dorna
*Assistant Examiner* — Joshua Daryl D Lannu
(74) *Attorney, Agent, or Firm* — Seckel IP, PLLC

(57) ABSTRACT

The method of modulating epileptogenicity in a brain of an epileptic patient includes: providing a virtual brain; provid-
(Continued)

ing a model of an epileptogenic and of a propagation zones and loading the models in the virtual brain to create a virtual epileptic brain; acquiring data of the brain of the epileptic patient; identifying, in the data, a location of at least one possible epileptogenic zone; fitting the virtual epileptic brain against the data acquired from the epileptic patient and parametrizing the at least one possible epileptogenic zone in the virtual epileptic brain as an epileptogenic zone; and simulating, within the virtual epileptic brain, the effect of a network modulation mimicking a clinical intervention of the brain of the patient.

18 Claims, 8 Drawing Sheets

(51) Int. Cl.
  *A61B 5/369* (2021.01)
  *A61B 34/10* (2016.01)
  *G16H 10/60* (2018.01)
  *G16H 50/50* (2018.01)

(52) U.S. Cl.
  CPC ........ *G16H 50/50* (2018.01); *A61B 2034/101* (2016.02); *A61B 2034/105* (2016.02); *G16H 10/60* (2018.01)

(56) References Cited

U.S. PATENT DOCUMENTS

| | | | |
|---|---|---|---|
| 2014/0222738 A1* | 8/2014 | Joyce | G06N 3/10 |
| | | | 706/47 |
| 2015/0164431 A1* | 6/2015 | Terry | A61B 5/4094 |
| | | | 600/300 |
| 2016/0183828 A1* | 6/2016 | Ouyang | G16H 50/20 |
| | | | 600/544 |
| 2018/0240549 A1 | 8/2018 | Terry et al. | |
| 2018/0279939 A1 | 10/2018 | Madsen et al. | |

FOREIGN PATENT DOCUMENTS

| | | |
|---|---|---|
| JP | 2014522283 A | 9/2014 |
| WO | 2012/151453 A2 | 11/2012 |
| WO | 2012170876 A2 | 12/2012 |
| WO | 2017/182637 A2 | 10/2017 |

OTHER PUBLICATIONS

Sinha et al., "An in silico approach for pre-surgical evaluation of an epileptic cortex", IEEE, 2014, pp. 4884-4887; cited in the ISR of parent U.S. Appl. No. 16/316,803.

Proix et al., "Individual structural connectivity defines propagation networks in partial epilepsy", arxiv.org/ftp/arxiv/papers/1604/1604.08508.pdf, Apr. 28, 2016 (retrieved Apr. 18, 2017); 30 pages; cited in the ISR of parent U.S. Appl. No. 16/316,803); parent U.S. Appl. No. 16/316,803.

Sanz Leon et al., "The Virtual Brain: a simulator of primate brain network dynamics", Frontiers in Neuroinformatics, vol. 7, Article 10, Jun. 2013, pp. 1-23; cited in the Specification.

Jirsa et al., "On the nature of seizure dynamics", Brain, vol. 137, 2014, pp. 2210-2230; cited in the Specification.

Proix et al., "Permittivity Coupling across Brain Regions Determines Seizure Recruitment in Partial Epilepsy", The Journal of Neuroscience, vol. 34, No. 45, Nov. 5, 2014, pp. 15009-15021; cited in the Specification.

International Search Report and Written Opinion dated Apr. 28, 2017 in corresponding application No. PCT/IB2016/001164 of parent U.S. Appl. No. 16/316,803 (in English; 10 pages).

Japanese Office Action dated Jun. 9, 2020 in counterpart JP Appl. No. 2019-503484 of parent U.S. Appl. No. 16/316,803; w/English machine translation (total 6 pages).

* cited by examiner

METHOD OF MODULATING EPILEPTOGENICITY IN A PATIENT'S BRAIN

This application is a divisional of U.S. application Ser. No. 16/316,803, U.S. national stage of PCT/IB2016/001164 filed Jul. 18, 2016, the content of each of which is hereby incorporated by reference herein in its entirety.

FIELD OF THE INVENTION

The invention relates to a method of modulating epileptogenicity in a patient's brain.

BACKGROUND OF THE INVENTION

Personalized medicine proposes the customization of healthcare with medical decisions, practices and products being tailored to an individual patient. Individual variability has clear effects upon the responsiveness to treatment approaches. Thus, diagnostic testing is often employed for selecting appropriate and optimal therapies based on the context of a patient's genetic content or other molecular and cellular analysis. Historically, personalized medicine uses heavily genetic information, but finds more and more viability on the systems level. Structural and functional neuroimaging play a key role and have already contributed concrete diagnostic tools that are though mostly restricted to neurology, such as presurgical evaluation of epilepsy or differential diagnosis of coma. Other domains such as psychiatry suffer from a void of diagnostic tools for routine clinical practice.

One solution to this issue is to link the interpretation of neuroimaging signals to computational brain models. So far, modeling has focused on reproducing the set of functionally active links between brain areas, but has been hampered by the stationary nature of most connectivity based metrics applied to validate the models. In fact, most meaningful situations and tasks in neuroscience pose themselves as non-stationary processes including the resting state, as well as cognitive and motor behaviors. The same applies to pathological behaviors also, of which seizure recruitment in epilepsy is one example.

In partial epilepsy, seizures originate in a local network, the so-called Epileptogenic Zone (EZ), before recruiting other brain regions, the so-called Propagation Zone (PZ). Correctly delineating the EZ is essential for successful interventions as, for example, resective surgery.

Accordingly, a need exists for identifying an EZ in the brain of an epileptic patient, and for modulating epileptogenicity in said patient's brain, which would allow a successful intervention of said patient.

SUMMARY OF THE INVENTION

The invention relates to a method of modulating epileptogenicity in a brain of an epileptic patient comprising the steps of: providing a virtual brain; providing a model of an epileptogenic and propagation zones and loading said models in the virtual brain to create a virtual epileptic brain; acquiring data of the brain of the epileptic patient; identifying, in said data, a location of at least one possible epileptogenic zone; fitting the virtual epileptic brain against the data acquired from the epileptic patient and parametrizing at least one possible subset of said epileptogenic zone in the virtual epileptic brain as an epileptogenic zone; and simulating, within the virtual epileptic brain, the effect of a network modulation mimicking a clinical intervention of the brain of the patient.

Preferentially, —the virtual brain is a computerized platform modelling various zones or nodes of a primate brain and connectivity between said zones or nodes; —the model of the epileptogenic zone is a mathematical model describing the onset, the time-course and the offset of epileptic discharges in said zone; —the mathematical model of the epileptogenic zone is defined by state variables describing fast discharges, defining spike and wave events in the discharges, and a variable being a slow permittivity variable, and differential equations; —the structural data comprise magnetic resonance imaging, diffusion-weighted magnetic resonance imaging, nuclear magnetic resonance imaging, and/or magnetic resonance tomography images data of the brain of the patient; —the method further comprises the step of reconstructing the patient brain in the virtual brain; —the method further comprises the step of identifying, in the acquired structural data of the patient brain, anomalies, and incorporating said anomalies in the virtual brain; —the method further comprises the step of identifying one or a plurality of possible propagation zones and of one or a plurality of possible other zones and parametrizing said possible propagation and other zones as propagation and other zones in the virtual brain; —for the parametrization of the possible epileptogenic, propagation and other zones, an excitability parameter characterizing the degree of epileptogenicity is used; —for the identification of the degree of epileptogenicity of epileptogenic and propagation zone, the excitability parameter is fit against functional patient data; a plurality of simulations is carried out for a plurality of possible epileptogenic zones, distributions of excitability parameters, and other network modulations including resections and stimulations, mimicking the effect of a clinical intervention.

BRIEF DESCRIPTION OF THE DRAWINGS

Other features and aspects of the present invention will be apparent from the following description and the accompanying drawings, in which.

DETAILED DESCRIPTION OF THE INVENTION

Figure 1:
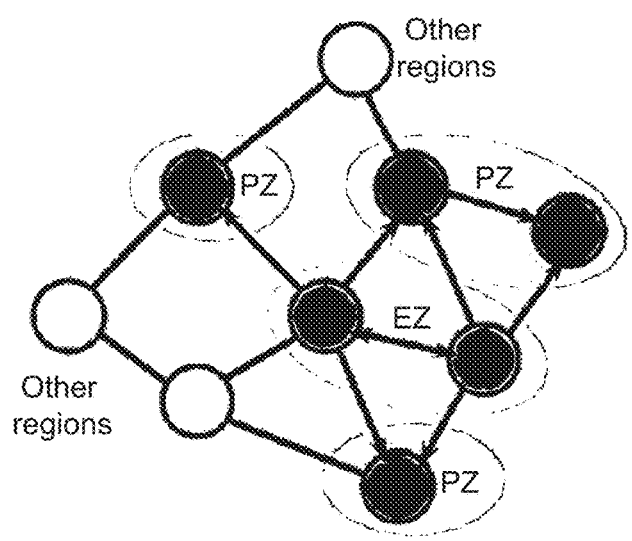
FIG. 1 represents a spatial distribution map of epileptogenicity, in a virtual brain network, for the implementation of the method according to the invention.

The invention relates to a method of reducing epileptogenicity in a patient's brain by identifying and modulating the epileptogenic zone.

Epilepsy is a group of neurological diseases characterized by epileptic seizures. Epileptic seizures are episodes that can vary from brief and nearly undetectable to long periods of vigorous shaking. In epilepsy, seizures tend to recur, and have no immediate underlying cause. The cause of most cases of epilepsy is unknown, although some people develop epilepsy as the result of brain injury, stroke, brain tumours, infections of the brain, and birth defects. Known genetic mutations are directly linked to a small proportion of cases. Epileptic seizures are the result of excessive and abnormal nerve cell activity in the cortex of the brain. Epilepsy can often be confirmed with an electroencephalogram (EEG). In partial epilepsy, seizures arise from a localized area or network, called the epileptogenic zone (EZ). They are called partial seizures. Partial seizures can be asymptomatic, and their spread to downstream brain regions is often linked to the emergence of clinical symptoms including cognitive impairment and loss of consciousness. How brain areas are recruited during seizure propagation is not well understood. Intracranial depth or stereotactic electroencephalograms (SEEGs) are commonly used to delineate the EZ in drug-resistant patient candidates for neurosurgery. In clinical practice, direct stimulation of brain regions with intracranial electrodes is used to localize epileptogenic regions and assess their degree of epileptogenicity. Time delays of seizure recruitment have also been considered to be indicative for the strength of epileptogenicity, but remain controversial as there is a large degree of spatial and temporal variation of propagation, even within the same patient. Seizure propagation from the epileptogenic zone toward neighboring zones has been observed experimentally.

According to a first step of the invention, a virtual brain is provided.

The virtual brain is a computerized platform modelling various zones or nodes of a primate brain and connectivity between said zones or nodes. An example of a virtual brain is disclosed in the publication document entitled "*The Virtual Brain: a simulator of primate brain network dynamics*", Paula Sanz Leon et al., 11 Jun. 2013, which is incorporated herein, by citation of reference. In this document, the virtual brain is disclosed as a neuro-informatics platform for full brain network simulations using biologically realistic connectivity. This simulation environment enables the model-based inference of neurophysiological mechanisms across different brain scales that underlie the generation of macroscopic neuroimaging signals including functional Magnetic Resonance Imaging (fMRI), EEG and Magnetoencephalography (MEG). It allows the reproduction and evaluation of personalized configurations of the brain by using individual subject data.

According to a further step of the invention, a model of an epileptogenic zone (EZ) and a model of the propagation of an epileptic discharge from an EZ to a propagation zone (PZ) are provided, and loaded in the virtual brain.

The model of the epileptogenic zone is a mathematical model describing the onset, the time-course and the offset of epileptic discharges in said zone. Such a model is disclosed, for example, in the publication document entitled "*On the nature of seizure dynamics*", Jirsa et al., Brain 2014, 137, 2210-2230, which is incorporated herein, by citation of reference. This model is named Epileptor. It comprises five state variables acting on three different time scales. On the fastest time scale, state variables $x_1$ and $y_1$ account for the fast discharges during the seizure. On the slowest time scale, the permittivity state variable z accounts for slow processes such as variation in extracellular ion concentrations, energy consumption, and tissue oxygenation. The system exhibits fast oscillations during the ictal state through the variables $x_1$ and $y_1$. Autonomous switching between interictal and ictal states is realized via the permittivity variable z through saddle-node and homoclinic bifurcation mechanisms for the seizure onset and offset, respectively. The switching is accompanied by a direct current (DC) shift, which has been recorded in vitro and in vivo. On the intermediate time scale, state variables $x_2$ and $y_2$ describe the spike-and-wave electrographic patterns observed during the seizure, as well as the interictal and preictal spikes when excited by the fastest system via the coupling $g(x_1)$. The equations of the model read as follows:

$$\dot{x}_1 = y_1 - f_1(x_1, x_2) - z + I_1$$

$$\dot{y}_1 = 1 - 5x_1^2 - y_1$$

$$\dot{z} = \frac{1}{\tau_0}(4(x_1 - x_0) - z)$$

$$\dot{x}_2 = -y_2 + x_2 - x_2^3 + I_2 + 0.002 g(x_1) - 0.3(z - 3.5)$$

$$\dot{y}_2 = \frac{1}{\tau_2}(-y_2 + f_2(x_1, x_2))$$

where $$f_1(x_1, x_2) = \begin{cases} x_1^3 - 3x_1^2 & \text{if } x_1 < 0 \\ (x_2 - 0.6(z-4)^2)x_1 & \text{if } x_1 \geq 0 \end{cases}$$

$$f_2(x_1, x_2) = \begin{cases} 0 & \text{if } x_2 < -0.25 \\ 6(x_2 + 0.25)x_1 & \text{if } x_2 \geq -0.25 \end{cases}$$

$$g(x_1) = \int_{t_0}^{t} e^{-\gamma(t-\tau)} x_1(\tau) d\tau$$

and $x_0=-1.6$; $\tau_0=2857$; $\tau_2=10$; $I_1=3.1$; $I_2=0.45$; $\gamma=0.01$. The parameter $x_0$ controls the tissue excitability, and is epileptogenic triggering seizures autonomously, if $x_0$ is greater than a critical value, $x_{0C}=-2.05$; otherwise the tissue is healthy. $I_1$ and $I_2$ are passive currents setting the operating point of the model.

The model of the propagation zone is identical to the one of an EZ, however with an excitability parameter inferior to the critical value $x_{0C}=-2.05$. All other brain areas may be modelled by Epileptors with excitability values far from the threshold, or equivalently standard neural population models as disclosed in Paula Sanz Leon et al., 11 Jun. 2013, which is incorporated herein, by citation of reference. The coupling between brain areas follows a mathematical model as disclosed in the publication document entitled "*Permittivity Coupling across Brain Regions Determines Seizure Recruitment in Partial Epilepsy*", Timothée Proix et al., The Journal of Neuroscience, Nov. 5, 2014, 34(45):15009-15021, which is incorporated herein, by citation of reference. Permittivity coupling quantifies the influence of neuronal fast discharges $x_{1j}$ of a remote region j on the local slow permittivity variable of a region i. Changes in ion homeostasis are influenced by both local and remote neuronal discharges via a linear difference coupling function, which quantifies the deviation from the interictal stable state as a perturbation perpendicular to the synchronization manifold. The linearity is justified as a first order approximation of the Taylor expansion around the synchronized solution. Permittivity coupling further includes the connectome $C_{ij}$, a scaling factor G, which both are absorbed in $K_{ij}=GC_{ij}$. The permittivity coupling from area j to area i reads $\Sigma_{j=1}^{N}K_{ij}\cdot(x_{1,j}(t-\tau_{ij})-x_{1,i}(t))$ where $\tau_{ij}$ denotes the signal transmission delay.

When loading the models of the epileptogenic zone (EZ) and propagation zone (PZ) in the virtual brain, the signal transmission time delays are here neglected, because synchronization effects will not be considered, but rather only the epileptic spread, which is determined by the slow dynamics of the permittivity coupling. Mathematically, the virtual brain then corresponds to the following equations:

$$\dot{x}_{1,i} = y_{1,i} - f_1(x_{1,i}, x_{2,i}) - z + I_{1,i}$$

$$\dot{y}_{1,i} = 1 - 5(x_{1,i})^2 - y_{1,i}$$

$$\dot{z}_i = \frac{1}{\tau_0}\left(4(x_1 - x_0) - z_i - \sum_{j=1}^{N}K_{ij}\cdot(x_{1,j} - x_{1,i})\right)$$

$$\dot{x}_{2,i} = -y_{2,i} + x_{2,i} - (x_{2,i})^3 + I_{2,i} + 0.002\, g(x_{1,i}) - 0.3(z_i - 3.5)$$

$$\dot{y}_{2,i} = \frac{1}{\tau_2}(-y_{2,i} + f_2(x_{1,i}, x_{2,i}))$$

According to a further step of the invention, structural and functional data of the brain of the epileptic patient are acquired. Structural data are for example images data of the patient brain acquired using magnetic resonance imaging (MRI), diffusion-weighted magnetic resonance imaging (DW-MRI), nuclear magnetic resonance imaging (NMRI), or magnetic resonance tomography (MRT). Functional data are for example electroencephalographic signals of the patient brain acquired through EEG or SEEG techniques.

According a further step of the invention, a structural reconstruction of the patient brain is carried out in the virtual brain, using the structural data acquired for said patient brain.

Indeed, the non-invasive structural neuroimaging using MRI and dMRI allows reconstruction of the patient's individual brain network topography and connection topology within a 3D physical space of the virtual brain.

Preferentially, the structural anomalies identified in the patient brain structural data are incorporated into the virtual brain.

Indeed, dramatic structural changes are induced by anomalies changing the topology of the structural network and thus altering the dynamical properties of the seizure recruitment.

The structural anomalies are, for example, malignant or non-malignant brain tumours including hamartoma, strokes, pachygyria.

They generally appear as white or dark spots in the MRI images.

According to a further step of the invention, the location of one or a plurality of possible epileptogenic zones, one or a plurality of possible propagation zones and of one or a plurality of possible other zones are initially identified in the functional data of the patient brain, and corresponding zones are parametrised as epileptogenic, propagation or other zones in the virtual brain. This initial parameter setting serves as a prior for the subsequent data fitting procedures.

Indeed, non-invasive functional neuroimaging informs the clinician expert on the evolution of the epileptic seizure and allows the formulation of hypotheses on the location of the EZ, i.e. the hypothetical area in the brain responsible for the origin and early organisation of the epileptic activity. The PZ comprises areas that are recruited during the seizure evolution, but that are by themselves not epileptogenic. Parameters are initially set in the virtual brain network model following the hypothesis on the EZ. Practically, a spatial map of epileptogenicity is defined in the virtual brain, as shown in FIG. 1. In this map, each node is characterized by an excitability value $x_0$, which quantifies the ability of the model of a zone to trigger a seizure. For an isolated zone, G=0, the model can trigger seizures autonomously if $x_0 > x_{0C}$ and is referred to as epileptogenic. Inversely, if $x_0 < x_{0C}$, the model does not trigger seizures autonomously and is not epileptogenic. The spatial map of epileptogenicity comprises the excitability values of the EZ, the PZ and all other zone. Of course, only the nodes in the EZ discharge autonomously while embedded in the virtual brain.

The subsequent data fitting is thus carried out, the target for said data fitting being the excitability parameter $x_0$, which is estimated using automated approaches. Obtaining such estimates of the parameters of the network model, given the available functional data is performed within a Bayesian framework, using a reduced Epileptor model and reduced functional data set for the fitting. The SEEG data are windowed and Fourier transformed to obtain estimates of their spectral density over time. Then SEEG power above 10 Hz is summed to capture the temporal variation of the fast activity. These time series are corrected to a preictal baseline, log-transformed and linearly detrended over the time window encompassing the seizure.

Hidden states in Bayesian modeling represent states of the generative model that are not directly observable. Uninformative priors are placed on the hidden states' initial conditions, while their evolution follows a Euler-Maruyama discretization of the corresponding stochastic differential equations with linear additive normally distributed noise. Uninformative priors are placed on the excitability parameter per node $x_0$, observation baseline power, scale and noise. Finally, the length of the seizure is also allowed to freely vary to match that of a given recorded seizure. Structural connectivity specifies a gamma prior on the connectivity used in the generative method. This model is implemented using a software for Bayesian inference, which implements both Hamiltonian Monte-Carlo and automatic variational inference algorithms for generic differential probability models. This approach takes advantage of the efficiency of the variational algorithm, which constructs an approximate proxy distribution on the true posterior optimized via stochastic gradient ascent.

According to further steps of the invention, a simulation of the propagation of an epileptic discharge from said possible epileptogenic zone to other zones is carried out in the virtual brain under systematic variation of model parameters. These parameter variations correspond to network modulations that may have inverse effects upon the seizure numbers in different brain regions and are thus non-trivial. Systematic simulations and quantifications of these modulation effects provide parameter spaces indicating the number of seizures in the virtual brain and the extent of seizure propagation. Changes in parameters are directly linked to therapeutic network interventions, though the link is not always evident, since the variation of a network parameter may find different realizations in clinical practice. For instance, the excitability of a brain region in the network node model is a key parameter, which is physiologically linked to variables such as balance of excitation and inhibition, local synaptic efficacy, extracellular ionic concentrations, or glial activity. Alterations of these variables will result in excitability changes in the tissue, and thus in the desired network effects predicted by the virtual brain model.

Practically, the patient's brain network model is evaluated via simulation, data fitting and mathematical analysis. It is used to "fingerprint" individual patient brains by identifying a personalized parameter set through data fitting. Systematic computational simulations further generate parameter maps outlining the zones of seizures and seizure freedom. These maps will give guidance of how to tune model parameters. The result of this evaluation predicts the most likely propagation patterns through the patient's brain and allows the exploration of brain intervention strategies.

The method according to the invention improves the surgical outcome. First, following non-invasive EEG/MEG and invasive SEEG exploration, the EZ hypotheses are fit to the data and improved. Second, systematic network modulations mimick clinical interventions strategies and can be used to identify novel therapeutic strategies. Modulations include stimulation paradigms, lesioning of network links, resections of brain areas and changes of local brain region parameters such as excitability. For instance, surgical strategies are tested within the virtual brain. So far, traditional approaches to surgery apply one focal resection or ablation at the hypothesized EZ, based on the dogmatic concept that medically refractory epilepsy is ultimately a focal disease. A large unknown remains the size, the number and the specific anatomical location of possible resections or thermal lesions designed to modulate large-scale epileptic networks. The invention allows not only to parametrically vary the size of the resection focus, but also to employ multiple lesions at different locations making thus full use of the network nature of the virtual epileptic brain model. Technically, this is possible nowadays: stereotactic-guided laser technology, for instance, permits the modulation of large-scale networks by allowing the placement of multiple lesions in key components of previously mapped epileptic networks.

Example: Identification of an Epileptogenic Zone in the Brain of a Patient Diagnosed with Bitemporal Epilepsy A right-handed 41-year-old female patient initially diagnosed with bitemporal epilepsy underwent comprehensive presurgical evaluation, including clinical history, neurological examination, neuropsychological testing, structural and diffusion MRI scanning, EEG and SEEG recordings along with video monitoring. Nine SEEG electrodes were placed in critical regions based for the presurgical evaluation. SEEG electrodes comprised 10 to 15 contacts. Each contact is 2 mm of length, 0.8 mm in diameter and is 1.5 mm apart from other contacts. Brain signals were recorded using a 128-channel Deltamed™ system (sampling rate: 512 Hz, hardware band-pass filtering: between 0.16 and 97 Hz). Structural and diffusion MRI were acquired with a Siemens™ Magnetom™ Verio™ 3T Scanner. T1-weighted images were acquired with a MPRAGE-sequence (TR=1900 ms, TE=2.19 ms, voxel size=1×1×1 mm3, 208 slices). The diffusion acquisition used a DTI-MR sequence (angular gradient set of 64 directions, TR=10.7 s, TE=95 ms, 70 slices, voxel size=2×2×2 mm3, b-value=1000 s/mm2).

Structural reconstruction was then carried out. The large-scale connectivity and the cortical surface of the patient were reconstructed using SCRIPTS™, a processing pipeline tailored for the virtual brain. The brain is divided in several regions according to a parcellation template, which is used for whole brain tractography to develop the connectivity and delay matrices. Cortical and subcortical surfaces are reconstructed and downsampled, along with a mapping of vertices to corresponding region labels. All processed data are formatted to facilitate import into the virtual brain.

Figure 2A:
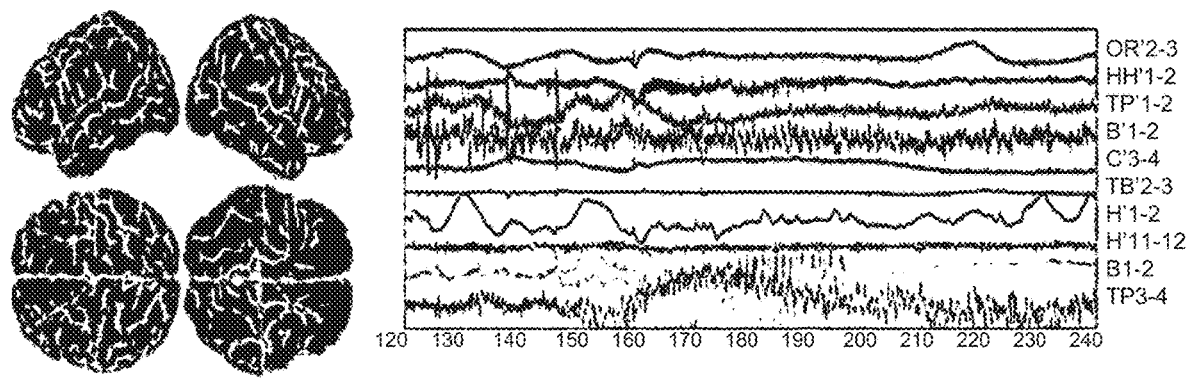
FIGS. 2A and 2B show, respectively, a simple and a complex epileptic seizures that have been recorded for an epileptic patient for the implementation of the method according to the invention.
Figure 2B:
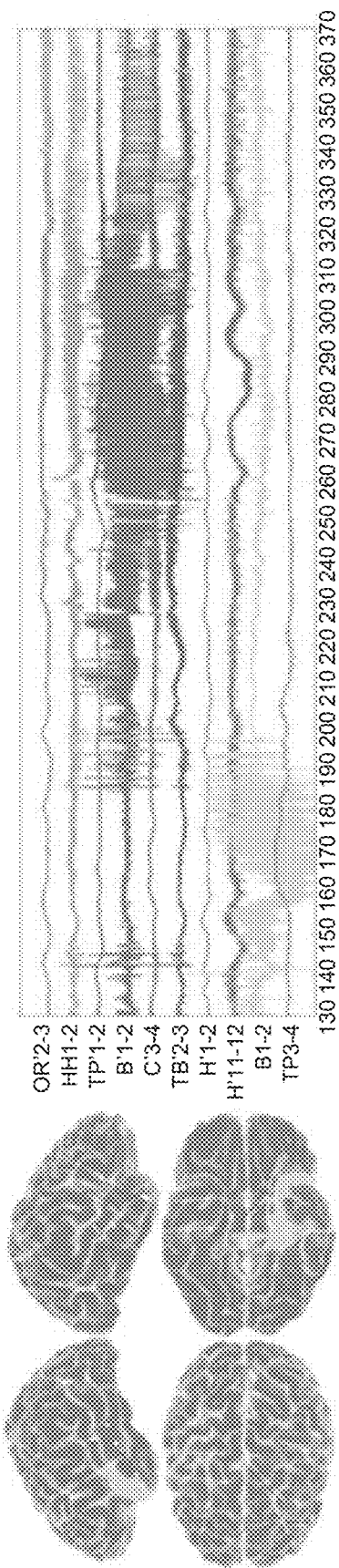

The MRI examination revealed a hypothalamic hamartoma. Surface EEG recordings revealed interictal spikes and indicated a bias towards the left hemisphere. Based on the presurgical evaluation, seven SEEG electrodes were implanted in the left hemisphere, and two in the right hemisphere. One electrode was implanted in the hypothalamic hamartoma. FIGS. 2A and 2B show the implantation scheme in the left column. During two weeks of continuous SEEG recordings, 6 simple seizures localized in the right hippocampus and two complex seizures starting in the right hippocampus and then recruiting the left hippocampus, the left temporal lobe and the hypothalamic hamartoma were recorded. Representative seizure propagation patterns are shown in FIGS. 2A and 2B.

This structural anomaly was integrated into the model. Here, a hypothalamic hamartoma was integrated via a modification of the local connectivity $K_{ij}=G_{hyp}C_{ij}$ of the hypothalamus. This hamartoma was delineated in the MRI scan. It was used as a seed region of interest to reconstruct the local connectivity. The local connectivity strength was scaled up parametrically by the scalar factor $G_{hyp}$ to quantify the effect of the hamartoma without changing its local connection topology.

Each node of the virtual brain network was loaded with the Epileptor model. The nodes were connected via permittivity coupling, which acts on a slow time scale and allow the spread of the seizure through the network by recruiting regions not in the EZ. The excitability parameters for EZ, PZ and all other regions according to clinical criteria comprising (i) regions involved in the seizure; (ii) seizure length; (iii) length of time delays before recruitment of other regions; (iv) seizure frequency in each region, were set. The spatial distribution of excitability was then heterogeneous across the network, with high value of excitability for regions in the EZ ($x_0 > x_{0C}+0.4$), smaller excitability values for regions in the PZ ($x_{0C}+0.4 > x_0 \geq x_{0C}$), and other nodes not epileptogenic ($x_0 < x_{0C}$). Once EZ and PZ were defined, the systematic network modulation was performed using a parameter space exploration by varying the following parameters: (i) the global coupling strength G, which is a scalar factor multiplying the whole connectivity matrix, (ii) the local coupling strength of the hypothalamus $G_{hyp}$, which is a scalar factor multiplying the contribution of the hypothalamus to the connectivity matrix, (iii) the excitability values $x_0^{right\ hippocampus}$ of the right hippocampus, (iv) the excitability values $x_0^{Other\ regions}$ of the regions not recruited in the propagation zone. The excitability values of the other regions in the EZ and the PZ were fixed as in Table 1 hereunder where $x_0 = x_{0C} + \Delta_{x_0}$.

| Name of the region | $\Delta x_0$ | Zones |
| --- | --- | --- |
| Right hippocampus | 1.3 | EZ |
| Left hippocampus | 0.4 | EZ |
| Left hypothalamus | 0.4 | EZ |
| Right hypothalamus | 0.4 | EZ |
| Brain Stem | 0.31 | PZ |
| Left parahippocampal | 0.27 | PZ |
| Left thalamus | 0.24 | PZ |
| Left temporal pole | 0.16 | PZ |
| Other regions | −0.2 | Other regions |

Figure 3A:
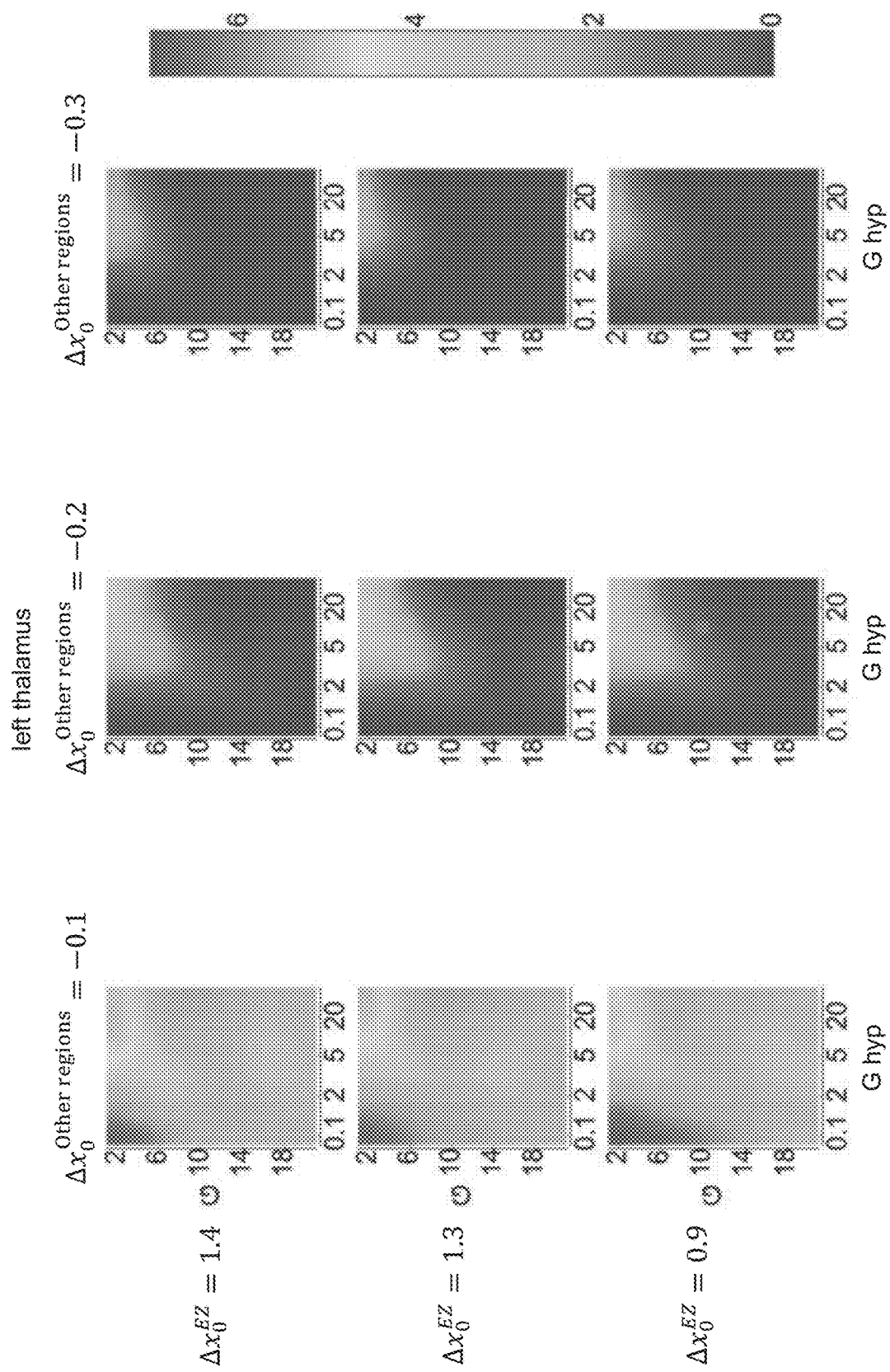
FIGS. 3A, 3B and 3C are navigation charts that relate to, respectively, the left thalamus, the left hypothalamus and the left fusiform cortex providing from simulations of epileptic discharges according to the method of the invention.
Figure 3B:
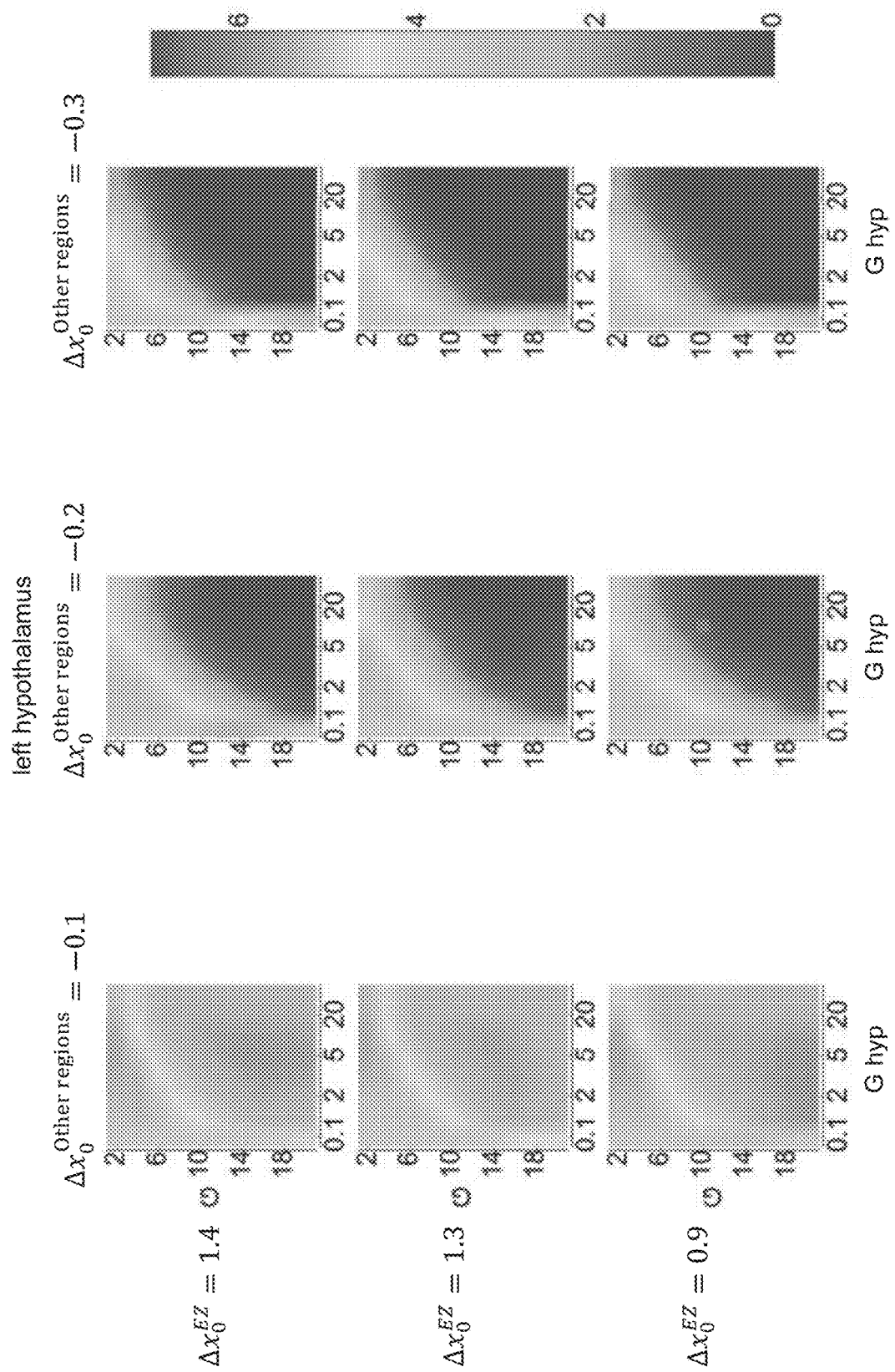
Figure 3C:
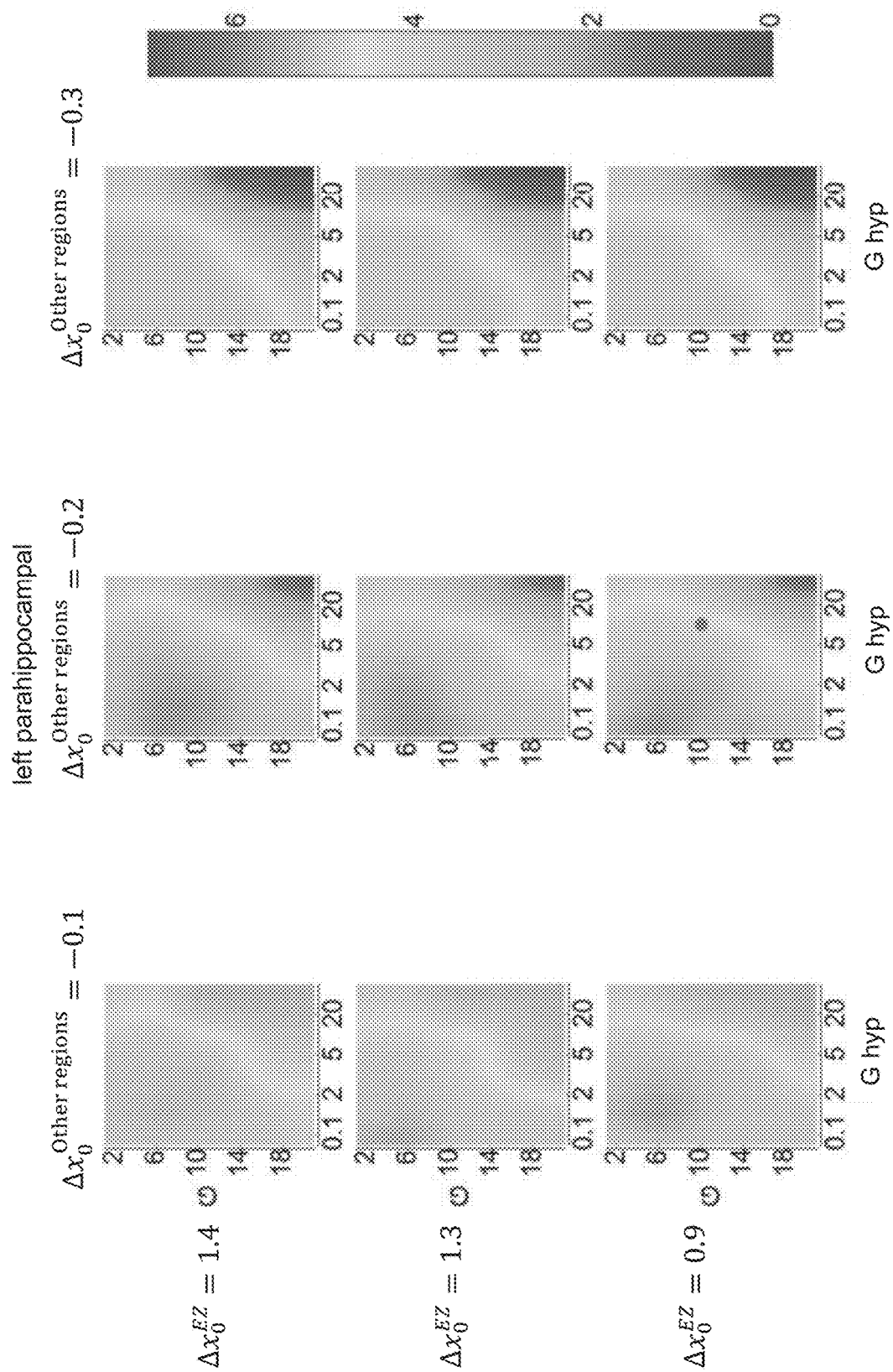

To describe the virtual brain network behaviour in the thus four-dimensional parameter space, the clinical criteria i)

through iv) for seizure quantification were used. FIGS. 3A to 3C show one of these quantifiers, the frequency of recruitment for three different regions in a seizure over a fixed simulation time as a function of the four parameters G, $G_{hyp}$, $x_0^{right\ hippocampus}$ and $x_0^{Other\ regions}$. They illustrate the results of the systematic parameter space explorations. These navigation charts offer the clinician a tool for decision-making and hypothesis building. For instance, the figures demonstrate for this particular patient that changes of excitability in the EZ regions show fairly little influence on the number of seizures in the VEP brain model, whereas reduction of excitability outside of EZ/PZ regions is linked to seizure reduction in the left thalamus and hypothalamus, and to a lesser extent in the left parahippocampus (FIGS. 3A and 3B). A decrease of left hypothalamic connectivity will always cause an increase of seizures in the left hypothalamus, but not the left thalamus. The only means of increasing the likelihood for seizures in the left thalamus is the increase of the scaling of global coupling G, while maintaining high values of hypothalamic connectivity (FIG. 3A). For all of the above scenarios, the left parahippocampus shows fairly high seizure numbers with one exception, that is high hypothalamic connectivity and low overall strength of global coupling G (FIG. 3C).

Figure 4A:
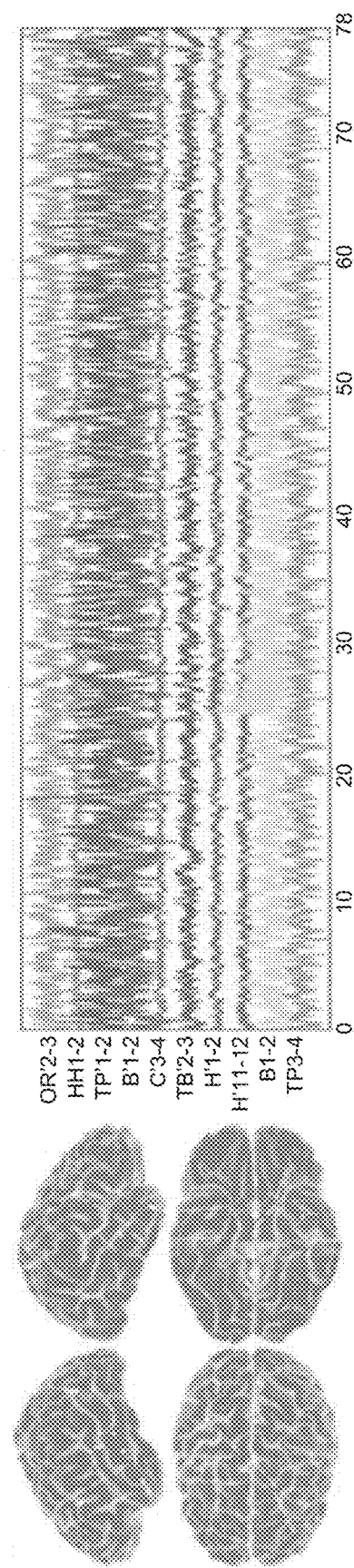
FIGS. 4A and 4B show, respectively, simulations of a simple and a complex epileptic seizures generated with similar regions recruited compared to the real SEEG recordings of FIGS. 2A and 2B.
Figure 4B:
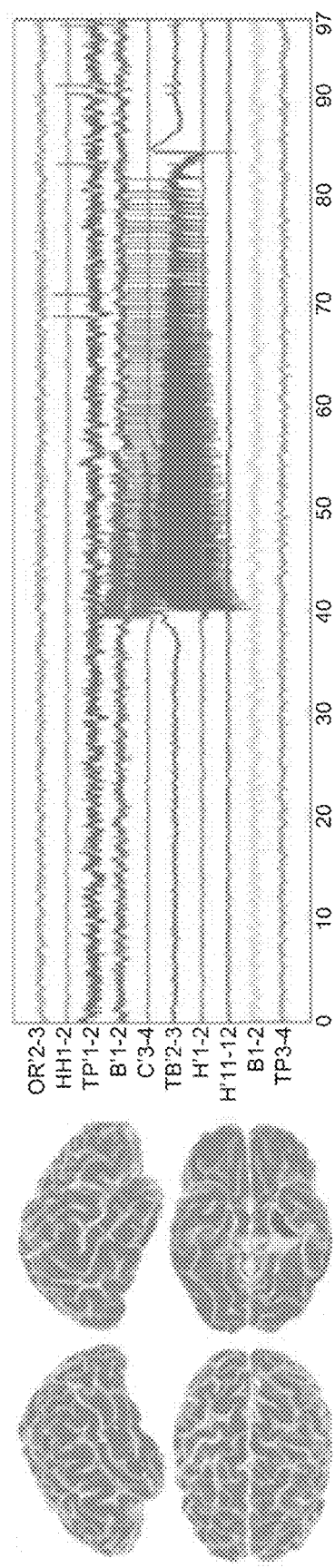

A representative set of parameters (G=10, $G_{hyp}$=10, $\Delta x_0^{right\ hippocampus}$=1.3, $\Delta x_0^{Other\ regions}$=−0.2) were selected corresponding to the dot in FIGS. 3A to 3C matching the patient's seizure with regard to the clinical criteria i) through iv). The virtual brain network model was simulated over a period of 20 seizures and computed the forward solution for the SEEG electrodes. Simple seizures and complex seizures were generated with similar regions recruited compared to the real SEEG recordings of FIGS. 2A and 2B. These seizures are shown in FIGS. 4A and 4B.

Figure 5A:
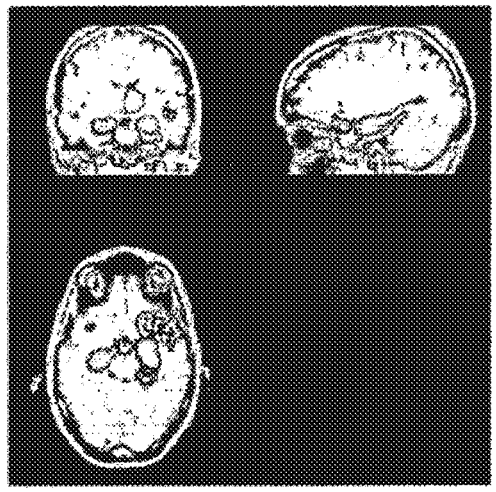
FIGS. 5A, 5B and 5C are images showing, respectively, the clinician's prediction of epileptogenic and propagation zones in a patient's brain, a first simulation of such zones in the virtual brain, and a second simulation of such zones in said virtual brain obtained using a prior data fitting, according to the method of the invention.
Figure 5B:
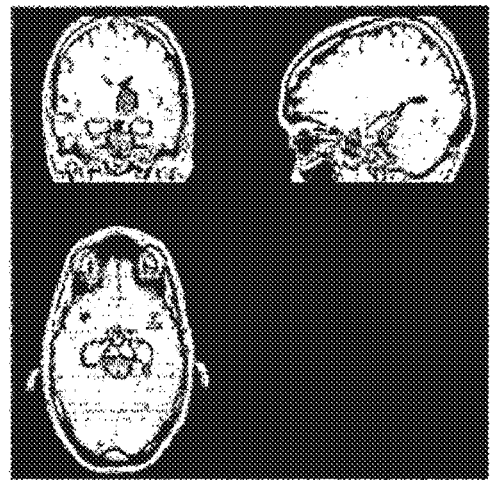
Figure 5C:
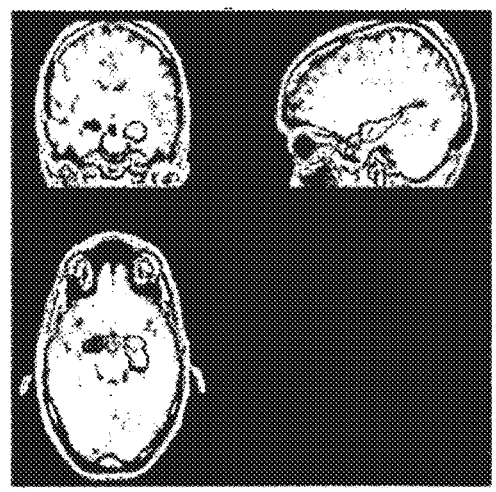

FIG. 5A shows the spatial extent of the EZ and the PZ such as estimated by clinician expertise. FIG. 5B shows the spatial extent of the excitability zone expressed through the parameter distribution of $x_0=x_{0C}+\Delta x_0$ illustrated via its deviations $\Delta x_0$ from the critical value $x_{0C}$=−2.05. FIG. 5C shows the comparison of the distribution of excitabilities found by fitting the model to the SEEG data. In those figures, the EZ are represented in light clear zones. It appears that data fitting allows to identify a bilateral mesial temporal EZ, a result well in agreement with the clinical interpretation.

Figure 6A:
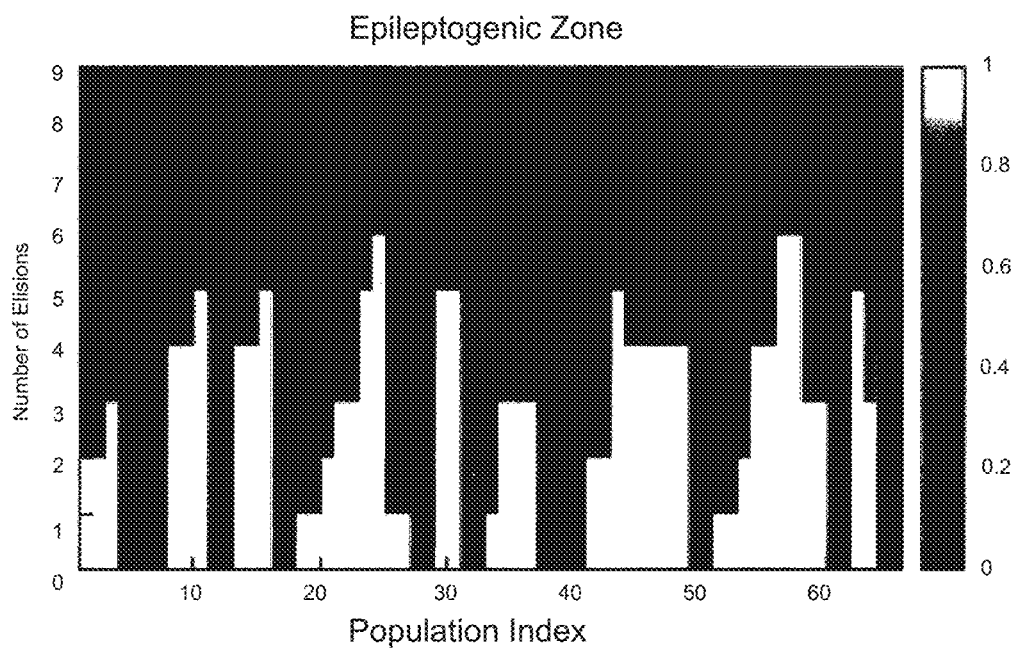
FIGS. 6A and 6B are graphs that demonstrate the capacity of the method according to the invention to identify minimally invasive approaches that may allow to stop epileptic seizure propagation.
Figure 6B:
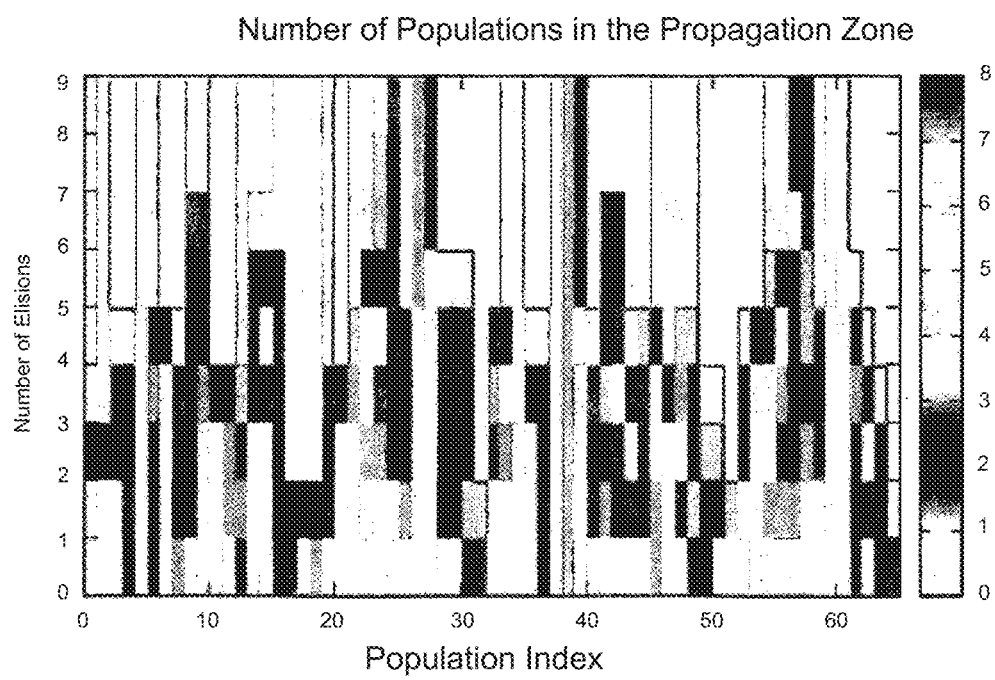

FIGS. 6A and 6B demonstrate the capacity of the invention to identify minimally invasive approaches to stop seizure propagation as a function of the epileptogenic zone. In FIG. 6A, the colour code (black/white) indicates seizure propagation (white) or not (black). In FIG. 6B, the size of the propagation zone is plotted as a function of the epileptogenic zone. For the virtual epileptic brain, a small number of lesions is sufficient to stop seizure propagation, up to 6 lesions as appearing in FIG. 6A. The PZ reduces to 0, 1 or 2 areas after 5 to 6 lesions. If the virtual brain's PZ is composed of 0 to 2 areas, the network is not able to recruit any other regions.

The invention claimed is:

1. A method of modulating epileptogenicity in a brain of an epileptic primate patient comprising the steps of:
   providing a virtual primate brain, the virtual primate brain being a computerized platform modelling various zones or nodes of a primate brain and connectivity between the zones or nodes;
   providing a model of an epileptogenic zone and of a propagation zone and loading the model in the virtual primate brain to create a virtual epileptic primate brain;
   acquiring structural data of the brain of the epileptic primate patient;
   reconstructing the epileptic patient brain in the virtual epileptic primate brain using the structural data;
   acquiring functional data of the brain of the epileptic primate patient;
   fitting the virtual epileptic primate brain against the functional data acquired from the brain of the epileptic primate patient; and
   simulating, within the virtual epileptic primate brain, an effect of a network modulation mimicking a clinical intervention of the brain of the epileptic primate patient.

2. The method according to claim 1, wherein the model comprises a mathematical model describing an onset, a time-course and an offset of epileptic discharges in the epileptogenic zone.

3. The method according to claim 2, wherein the mathematical model is defined by state variables describing fast discharges, defining spike and wave events in the fast discharges, and a variable which is a slow permittivity variable, and differential equations.

4. The method according to claim 3, wherein the structural data and/or the functional data acquired from the brain of the epileptic primate patient comprise magnetic resonance imaging, diffusion-weighted magnetic resonance imaging, nuclear magnetic resonance imaging, and/or magnetic resonance tomography images data of the brain of the epileptic primate patient.

5. The method according to claim 3, further comprising identifying, in the structural data and/or the functional data acquired from the brain of the epileptic primate patient, anomalies, and incorporating the anomalies in the virtual epileptic primate brain.

6. The method according to claim 3, further comprising identifying a location of one or a plurality of possible propagation zones and parameterizing the one or a plurality of possible propagation zones as propagation zones in the virtual epileptic primate brain.

7. The method according to claim 2, wherein the structural data and/or the functional data acquired from the brain of the epileptic primate patient comprise magnetic resonance imaging, diffusion-weighted magnetic resonance imaging, nuclear magnetic resonance imaging, and/or magnetic resonance tomography images data of the brain of the epileptic primate patient.

8. The method according to claim 2, further comprising identifying, in the structural data and/or the functional data acquired from the brain of the epileptic primate patient, anomalies, and incorporating the anomalies in the virtual epileptic primate brain.

9. The method according to claim 2, further comprising identifying a location of one or a plurality of possible propagation zones and parameterizing the one or a plurality of possible propagation zones as propagation zones in the virtual epileptic primate brain.

10. The method according to claim 1, wherein the structural data and/or the functional data acquired from the brain of the epileptic primate patient comprise magnetic resonance imaging, diffusion-weighted magnetic resonance imaging, nuclear magnetic resonance imaging, and/or magnetic resonance tomography images data of the brain of the epileptic primate patient.

11. The method according to claim 1, further comprising identifying, in the structural data and/or the functional data acquired from the patient of the epileptic primate patient, anomalies, and incorporating the anomalies in the virtual epileptic primate brain.

12. The method according to claim 1, further comprising identifying a location of one or a plurality of possible propagation zones and parameterizing the one or a plurality of possible propagation zones as propagation zones in the virtual epileptic primate brain.

13. The method according to claim 1, further comprising identifying in the structural data and/or the functional data acquired from the brain of the epileptic primate patient, a location of at least one possible epileptogenic zone and parameterizing the at least one possible epileptogenic zone in the virtual epileptic primate brain as a parameterized epileptogenic zone.

14. The method according to claim 13, wherein, for the parametrization of the at least one possible epileptogenic zone, an excitability parameter characterizing a degree of excitability of the at least one epileptogenic zone is used.

15. The method according to claim 14, wherein, for the parameterization of the one or a plurality of possible propagation zones as propagation zones, an excitability parameter characterizing the degree of excitability of the propagation zones is used.

16. The method according to claim 15, wherein, for an identification of the degree of excitability of the propagation zones, the excitability parameter is fit against the functional data acquired from the brain of the epileptic primate patient.

17. The method according to claim 14, wherein, for an identification of the degree of excitability of the at least one epileptogenic zone, the excitability parameter is fit against the functional data acquired from the brain of the epileptic primate patient.

18. The method according to claim 1, wherein a plurality of simulations is carried out for a plurality of possible epileptogenic zones.

\* \* \* \* \*